United States Patent [19]

Andrews et al.

[11] Patent Number: 5,807,707
[45] Date of Patent: Sep. 15, 1998

[54] HIGH EFFICIENCY TRANSLATION OF MRNA MOLECULES

[75] Inventors: David W. Andrews; Martin John Glenton Hughes, both of Hamilton; Akaterini Vassilakos, Toronto, all of Canada

[73] Assignee: McMaster University, Hamilton, Canada

[21] Appl. No.: 600,234

[22] Filed: Feb. 12, 1996

Related U.S. Application Data

[63] Continuation-in-part of Ser. No. 386,921, Feb. 10, 1995.

[51] Int. Cl.$^6$ .................... C12P 21/02; C07H 21/04; C12N 15/67
[52] U.S. Cl. ............ 435/69.1; 430/71.1; 430/71.2; 430/183; 536/23.1; 536/24.1; 536/24.2
[58] Field of Search .................. 435/69.1, 71.1, 435/71.2, 183; 536/23.1, 24.1, 24.2; 935/33, 34, 38, 44

[56] References Cited

U.S. PATENT DOCUMENTS

| | | | |
|---|---|---|---|
| 4,716,112 | 12/1987 | Panayotatos | 435/69.1 |
| 4,740,461 | 4/1988 | Kaufman | 435/69.1 |
| 5,079,159 | 1/1992 | Kaufman | 435/226 |
| 5,149,635 | 9/1992 | Gilles | 435/69.1 |
| 5,362,865 | 11/1994 | Austin | 536/24.1 |
| 5,378,619 | 1/1995 | Rogers | 435/172.3 |
| 5,424,412 | 6/1995 | Brown et al. | 536/24.1 |

OTHER PUBLICATIONS

Gallie et al. Gene 142 159–165, 1994.
Kruys et al. Proc. Natl. Acad. Sci 84 6030–6034, 1987.
Falcone et al. Mol. Cell Biol. 11(5) 2656–2664, 1991.
Sasavage et al. J. Biol. Chem. 257(2) 678–681, 1982.
Turner et al. J. Biol Chem 268(13) 9504–9510, 1993.
Grens et al. J Biol Chem 265(20)11810–11816, 1990.
Sheets et al. Genes & Devel. 8 926–938, 1994.
Gallie et al. Mol. Gen. Genet. 228 258–264, 1995.
Paris et al Mol. Cell Biol. 10 5634–5645, 1990.
Caput et al. Proc. Natl. Acad. Sc: 83–1670–1674, 1986.

*Primary Examiner*—Nancy Degen
*Attorney, Agent, or Firm*—Sim & McBurney

[57] ABSTRACT

An increased level of translation of a selected mRNA molecule is effected by coupling specific nucleotide sequences at the 5'- and 3'-ends of a nucleic acid molecule transcribable to or which itself is the mRNA molecule. The nucleotide sequence at the 5'-end is effective to increase the rate of translation initiation of the mRNA molecule in a cell while the nucleotide sequence at the 3'-end is effective to increase the period of translation of the mRNA molecule in a cell. The nucleotide sequence of the 3'-end is provided by a 3'-untranslated region (3'-UTR) of a gene, particularly that of β-prolactin, or an effective fragment thereof. A polyadenylation sequence preferably is provided at the 3'-end of the 3'-UTR sequence. The 3'-UTR sequence provides mRNA stabilization independent of the poly A tail.

37 Claims, 9 Drawing Sheets

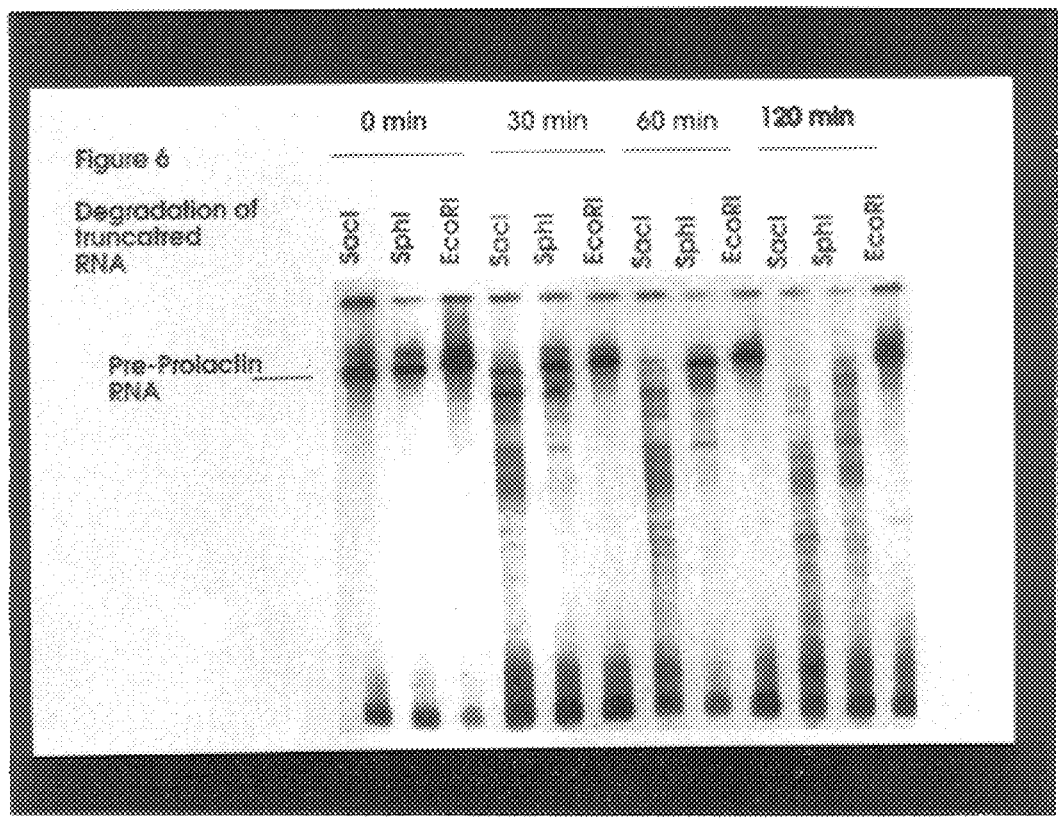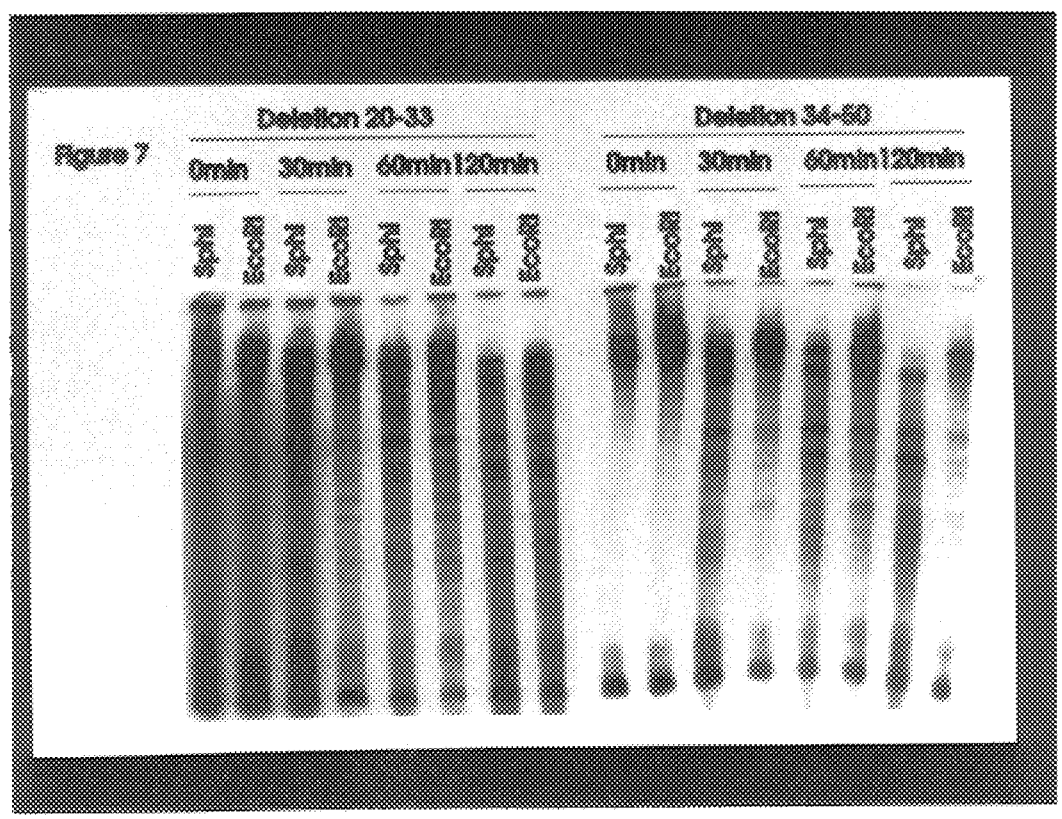

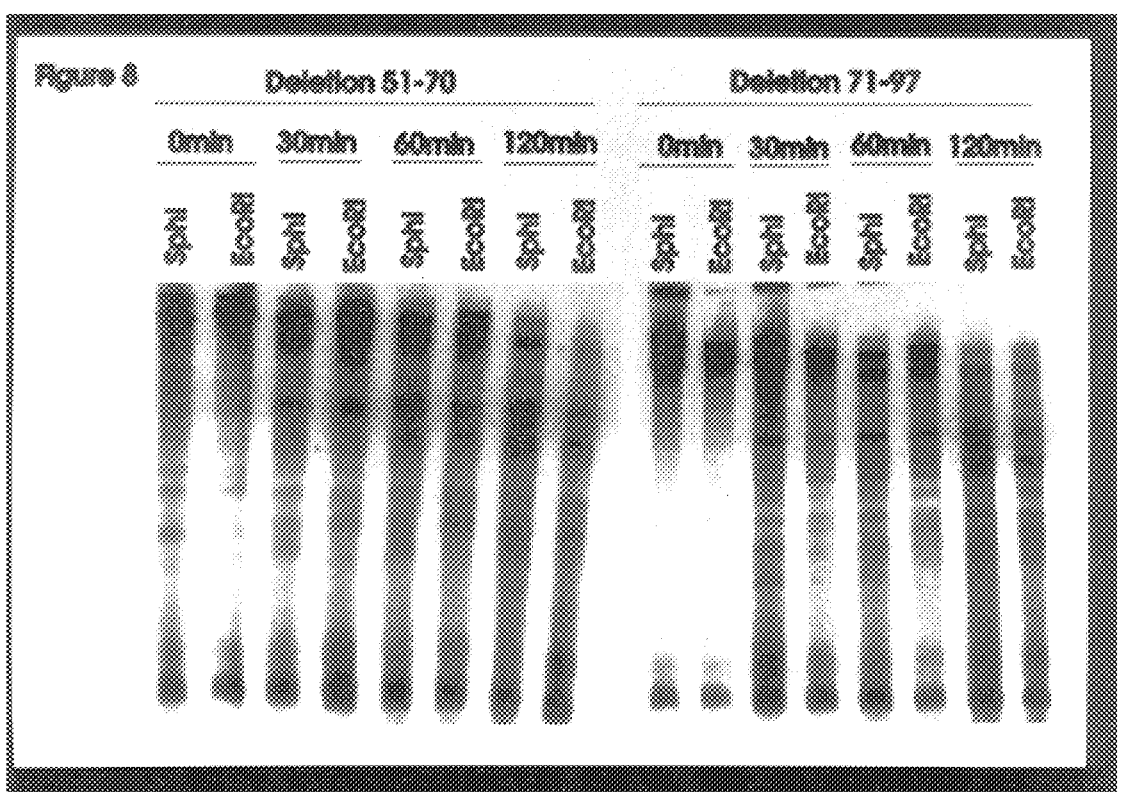

| LEADER NAME | LEADER SEQUENCE |
|---|---|

SD
ATTTAGGTGACACTATAGAATACAAGCTCATGG
  SP6 PROMOTOR                NCOI

KD
ATTTAGGTGACACTATAGAATACAAGCTGATCTACCATGG
  SP6 PROMOTOR                    NCOI

UTR
ATTTAGGTGACACTATAGAATACAAGCTTGCVTTGTTCTTTTTGCAGAAGCTCAGAATAAACGCTCAACTTTGGCAGATCCATGG
  SP6 PROMOTOR     HINDIII       XENOPUS B-GLOBIN 5' UTR                          NCOI

UTK
ATTTAGGTGACACTATAGAATACAAGCTTGCVTTGTTCTTTTTGCAGAAGCTCAGAATAAACGCTCAACTTTGGCAGATCTACCATGG
  SP6 PROMOTOR     HINDIII       XENOPUS B-GLOBIN 5' UTR                          BGLII  NCOI

FIG.9

Wild-type

Deletion, bases 51-70

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 236 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
AACAACAACU GCUAACGAGC UCGUAAGCCC ACAUUCCAUC CUUUCCAUUU CUGAGAUGGU    60
UCUUAAUGAU CCAUUCCCUG GCAAACUUCU CUGAGCUUUA UAGCUUUGUA AUGCAUGCUU   120
GGCUCUAAUG GGUUUCAUCU UAAAUAAAAA CAGACUCUGU AGCGAUGUCA AAAUCUAAAA   180
AAAAAAAAAA AAACCCCCCC CCCCUGCAGG UCGACUCUAG AGGAUCCCCG GAAUUC       236
```

( 2 ) INFORMATION FOR SEQ ID NO:2:

( i ) SEQUENCE CHARACTERISTICS:
    ( A ) LENGTH: 161 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2:

| | | | | | | |
|---|---|---|---|---|---|---|
| CGAGCUCGUA | AGCCCACAUU | CCAUCCUUUC | CAUUUCUGAG | AUGGUUCUUA | AUGAUCCAUU | 60 |
| CCCUGGCAAA | CUUCUCUGAG | CUUUAUAGCU | UUGUAAUGCA | UGCUUGGCUC | UAAUGGGUUU | 120 |
| CAUCUUAAAU | AAAAACAGAC | UCUGUAGCGA | UGUCAAAAUC | U | | 161 |

( 2 ) INFORMATION FOR SEQ ID NO:3:

( i ) SEQUENCE CHARACTERISTICS:
    ( A ) LENGTH: 47 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:3:

| | | | | |
|---|---|---|---|---|
| AUGAUCCAUU | CCCUGGCAAA | CUUCUCUGAG | CUUUAUAGCU | UUGUAAU | 47 |

( 2 ) INFORMATION FOR SEQ ID NO:4:

( i ) SEQUENCE CHARACTERISTICS:
    ( A ) LENGTH: 221 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:4:

| | | | | | | |
|---|---|---|---|---|---|---|
| CGAGCUCGUA | AGCCCACAUU | CCAUCCUUUC | CAUUUCUGAG | AUGGUUCUUA | AUGAUCCAUU | 60 |
| CCCUGGCAAA | CUUCUCUGAG | CUUUAUAGCU | UUGUAAUGCA | UGCUUGGCUC | UAAUGGGUUU | 120 |
| CAUCUUAAAU | AAAAACAGAC | UCUGUAGCGA | UGUCAAAAUC | UAAAAAAAAA | AAAAAAACC | 180 |
| CCCCCCCCU | GCAGGUCGAC | UCUAGAGGAU | CCCCGGAAUU | C | | 221 |

( 2 ) INFORMATION FOR SEQ ID NO:5:

( i ) SEQUENCE CHARACTERISTICS:
    ( A ) LENGTH: 138 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:5:

| | | | | | | |
|---|---|---|---|---|---|---|
| CGAGCUCGUA | AGCCCACAUU | CCAUCCUUUC | CAUUUCUGAG | AUGGUUCUUA | AUGAUCCAUU | 60 |
| CCCUGGCAAA | CUUCUCUGAG | CUUUAUAGCU | UUGUAAUGCA | UGCUUGGCUC | UAAUGGGUUU | 120 |
| CAUCUUAAAU | AAAAACAG | | | | | 138 |

( 2 ) INFORMATION FOR SEQ ID NO:6:

( i ) SEQUENCE CHARACTERISTICS:
    ( A ) LENGTH: 98 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:6:

| | | | | | | |
|---|---|---|---|---|---|---|
| CGAGCUCGUA | AGCCCACAUU | CCAUCCUUUC | CAUUUCUGAG | AUGGUUCUUA | AUGAUCCAUU | 60 |
| CCCUGGCAAA | CUUCUCUGAG | CUUUAUAGCU | UUGUAAUG | | | 98 |

( 2 ) INFORMATION FOR SEQ ID NO:7:

( i ) SEQUENCE CHARACTERISTICS:
        ( A ) LENGTH: 5 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

| | |
|---|---:|
| C G A G C | 5 |

( 2 ) INFORMATION FOR SEQ ID NO:8:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

| | |
|---|---:|
| CGAGCUCGUA AGCCCACAUU UCUGAGAUGG UUCUUAAUGA UCCAUCCCU GGCAAACUUC | 60 |
| UCUGAGCUUU AUAGCUUUGU AAUG | 84 |

( 2 ) INFORMATION FOR SEQ ID NO:9:

( i ) SEQUENCE CHARACTERISTICS:
        ( A ) LENGTH: 207 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

| | |
|---|---:|
| CGAGCUCGUA AGCCCACAUU UCUGAGAUGG UUCUUAAUGA UCCAUCCCU GGCAAACUUC | 60 |
| UCUGAGCUUU AUAGCUUUGU AAUGCAUGCU UGGCUCUAAU GGGUUUCAUC UUAAAUAAAA | 120 |
| ACAGACUCUG UAGCGAUGUC AAAAUCUAAA AAAAAAAAA AAAACCCCCC CCCCCUGCAG | 180 |
| GUCGACUCUA GAGGAUCCCC GGAAUUC | 207 |

( 2 ) INFORMATION FOR SEQ ID NO:10:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

| | |
|---|---:|
| CGAGCUCGUA AGCCCACAUU CCAUCCUUUC CAUAUGAUCC AUCCCUGGC AAACUUCUCU | 60 |
| GAGCUUUAUA GCUUUGUAAU G | 81 |

( 2 ) INFORMATION FOR SEQ ID NO:11:

( i ) SEQUENCE CHARACTERISTICS:
        ( A ) LENGTH: 204 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

| | |
|---|---:|
| CGAGCUCGUA AGCCCACAUU CCAUCCUUUC CAUAUGAUCC AUCCCUGGC AAACUUCUCU | 60 |
| GAGCUUUAUA GCUUUGUAAU GCAUGCUUGG CUCUAAUGGG UUUCAUCUUA AAUAAAACA | 120 |
| GACUCUGUAG CGAUGUCAAA AUCUAAAAAA AAAAAAAAA ACCCCCCCC CCUGCAGGUC | 180 |
| GACUCUAGAG GAUCCCCGGA AUUC | 204 |

( 2 ) INFORMATION FOR SEQ ID NO:12:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
CGAGCUCGUA  AGCCCACAUU  CCAUCCUUUC  CAUUUCUGAG  AUGGUUCUUA  CUUCUCUGAG     60
CUUUAUAGCU  UUGUAAUG                                                        78
```

( 2 ) INFORMATION FOR SEQ ID NO:13:

( i ) SEQUENCE CHARACTERISTICS:
        ( A ) LENGTH: 201 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
CGAGCUCGUA  AGCCCACAUU  CCAUCCUUUC  CAUUUCUGAG  AUGGUUCUUA  CUUCUCUGAG     60
CUUUAUAGCU  UUGUAAUGCA  UGCUUGGCUC  UAAUGGGUUU  CAUCUUAAAU  AAAAACAGAC    120
UCUGUAGCGA  UGUCAAAAUC  UAAAAAAAAA  AAAAAAAACC  CCCCCCCCU   GCAGGUCGAC    180
UCUAGAGGAU  CCCCGGAAUU  C                                                 201
```

( 2 ) INFORMATION FOR SEQ ID NO:14:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

```
CGAGCUCGUA  AGCCCACAUU  CCAUCCUUUC  CAUUUCUGAG  AUGGUUCUUA  AUGAUCCAUU     60
CCCUGGCAAA                                                                  70
```

( 2 ) INFORMATION FOR SEQ ID NO:15:

( i ) SEQUENCE CHARACTERISTICS:
        ( A ) LENGTH: 194 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

```
CGAGCUCGUA  AGCCCACAUU  CCAUCCUUUC  CAUUUCUGAG  AUGGUUCUUA  AUGAUCCAUU     60
CCCUGGCAAA  GCAUGCUUGG  CUCUAAUGGG  UUUCAUCUUA  AAUAAAAACA  GACUCUGUAG    120
CGAUGUCAAA  AUCUAAAAAA  AAAAAAAAAA  ACCCCCCCCC  CCUGCAGGUC  GACUCUAGAG    180
GAUCCCCGGA  AUUC                                                          194
```

( 2 ) INFORMATION FOR SEQ ID NO:16:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

```
ATTTAGGTGA  CACTATAGAA  TACAAGCTCA  TGG                                    33
```

( 2 ) INFORMATION FOR SEQ ID NO:17:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

```
ATTTAGGTGA CACTATAGAA TACAAGCTGA TCTACCATGG                              40
```

( 2 ) INFORMATION FOR SEQ ID NO:18:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

```
ATTTAGGTGA CACTATAGAA TACAAGCTTG CTTGTTCTTT TTGCAGAAGC TCAGAATAAA        60
CGCTCAACTT TGGCAGATCC ATGG                                               84
```

( 2 ) INFORMATION FOR SEQ ID NO:19:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

```
ATTTAGGTGA CACTATAGAA TACAAGCTTG CTTGTTCTTT TTGCAGAAGC TCAGAATAAA        60
CGCTCAACTT TGGCAGATCT ACCATGG                                            87
```

( 2 ) INFORMATION FOR SEQ ID NO:20:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

```
ACCAUGG                                                                   7
```

( 2 ) INFORMATION FOR SEQ ID NO:21:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

```
CCCAUGG                                                                   7
```

( 2 ) INFORMATION FOR SEQ ID NO:22:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

UGUAGCGAUG UCAAAAUAUU GUUGAAAGU                                                                29

HIGH EFFICIENCY TRANSLATION OF MRNA MOLECULES

REFERENCE TO RELATED APPLICATION

This application is a continuation-in-part of U.S. patent application Ser. No. 08/386,921 filed Feb. 10, 1995.

FIELD OF INVENTION

The present invention relates to the translation of messenger RNA (mRNA) molecules in cells and, in particular, to improvements in the efficiency thereof.

BACKGROUND TO THE INVENTION

The translational efficiency of mRNA has been shown to be due to several factors, including the 5' cap structure, the 5' leader sequence and sequences immediately surrounding the initiation codon (refs. 1 to 3—Throughout this specification, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure). These sequences largely determine both the rate and the fidelity of initiation of translation in vitro and in vivo. More recently sequences in the coding region have also been implicated in translational efficiency (refs. 4 to 12).

The relative abundance of an mRNA coding for a given gene product can also influence the amount of protein synthesized. The abundance of a specific mRNA species is determined both by the rate of transcript synthesis, processing and transport, as well as the translational half-life of the molecule within the cytoplasm (ref. 13). The translational half-life of an mRNA is determined by the kinetics of both mRNA inactivation (masking and unmasking) and degradation (chemical stability). The 3' untranslated region (UTR) of RNA molecules consists of a stretch of nucleotides usually containing methylation and polyadenylation sites. In most active cell systems, the RNA's are capped at the 3' end with a poly (A) stretch or tail. The UTR is thought to play several roles in translational regulation, including the control of translational initiation, control of translation during growth and differentiation of cells and RNA stability (ref. 14). In particular, the poly A tail, found on most eukaryotic mRNA species, has been shown to be a determinant of stability for many mRNAs (refs. 15 to 17). While there is evidence from involvement of polyadenylation in stabilizing transcripts in Xenopus oocytes, recent evidence also suggests that the poly A tail together with poly A binding protein may also be involved in increasing the efficiency of initiation for some mRNAs (refs. 15, 18 and 19). In addition, recent evidence suggests that polyadenylation and de-adenylation mechanisms are involved in the activation and inactivation of mRNA translation in oocytes (ref. 20).

Since most mRNAs routinely are polyadenylated, other mechanisms may contribute to the observed differences in the stability of certain mRNAs in eukaryotic cells. Evidence for gene specific regulatory mechanisms comes from the characterization of de-stabilization sequences in the 3' UTRs of cellular proto-oncogenes and of stabilization sequences present in the α- and β- globin 3' UTR (refs. 14 and 21).

In addition to providing insight into the mechanisms of translation, the analysis of UTR sequences has proven useful for the development of expression vectors capable of increasing the synthesis of foreign coding regions in vitro and in vivo (refs. 26 to 38). The inventors have previously described a semi-synthetic 5' leader sequence (termed UTK) containing the Xenopus β-globin 5' UTR fused to an appropriately positioned consensus sequence for translation initiation. The UTK leader has been found to improve the translation efficiency of every coding region tested to date, in both reticulocyte lysate (ref. 38) and wheat germ extract cell free translation systems.

It would be desirable to improve the level of translation of mRNA molecules in cells, particularly prokaryotic and eukaryotic cells.

SUMMARY OF INVENTION

The present invention provides a novel method for increasing the level of translation of MRNA molecules by the employment of a combination of specific nucleotide sequences operatively coupled to the 5' and 3' ends of mRNA molecules. The inventors have found, for the first time, that mRNA stabilization can be obtained independent of polyadenylation. This result is achieved by using the 3' UTR region of bovine preprolactin, although functionally-equivalent 3' UTR regions or fragments thereof may be employed.

Accordingly, in one aspect, the present invention provides a method of translating a selected mRNA molecule to provide an increased level of translation thereof, which comprises:

coupling to a nucleic acid molecule transcribable to or which itself is an mRNA molecule at the 5'-end thereof a first nucleotide sequence effective to increase the rate of translation initiation of the mRNA molecule in a cell, coupling to the nucleic acid molecule at the 3'-end thereof a second nucleotide sequence comprising at least a portion of a 3' untranslated region (UTR) of a gene and effective to increase the period of translation of the mRNA molecule in a cell, and effecting translation of the mRNA molecule in said cell.

In one embodiment of this aspect of the invention, the second nucleotide sequence comprises a nucleotide sequence the 3'-UTR of prolactin, as shown in FIG. 2 described below, including a segment thereof effective for maintaining RNA in translation-competent form, in particular, at least a portion of the 3'-UTR of prolactin contained within nucleotide 51 to nucleotide 97, more particularly, between nucleotides 81 and 98. Alternatively, the second nucleotide sequence nay comprise a nucleotide sequence of prolactin (selected from those shown in Table 1 below and effective to increase the period of translation), particularly the SphI or AlwHI 3'-truncation thereof. The sequence nucleotide sequence may further comprise a polyadenylation sequence attached to the 3' end thereof. As already noted above, the mRNA stabilization achieved by the 3' UTR sequence is independent of that provided by polyadenylation.

The first nucleotide sequence may comprise that of a β-globin 5'-UTR coupled to a translation initiation sequence particularly a Xenopus β-globin. The translation initiation sequence may comprise the Kozak consensus sequence AGNNAUGN, preferably the consensus sequence ANNAUGG, preferably the consensus sequence which is ACCAUGG (SEQ ID NO: 20). The initiation sequence may further comprise a Shine-Dalgarno sequence.

The translation of the selected mRNA molecule may be effected herein in any prokaryotic or eukaryotic cell, which may be E. coli and the Eubacteria, Bacillus, Salmonella, Staphylococcus, Mycobacteria, Streptomyces, Archebacteria, yeast, fungi, mammalian cells, such as CHO, Vero cells, MDCK, human diploid cells, BHK and HeLa cells, oocytes, and plant cells.

In another aspect of the invention, there is provided a method of translating a selected mRNA molecule, which comprises:

coupling to a nucleic acid molecule transcribable to or which itself is an mRNA molecule at the 3'-end thereof a nucleotide sequence of the 3'-UTR of prolactin effective to increase the period of translation of the mRNA molecule in a cell, and effecting translation of said mRNA molecule in said cell. A polyadenylation nucleotide sequence may be coupled to the 3' end of the nucleotide sequence of the 3'-UTR.

The present invention further includes a hybrid nucleic acid molecule, comprising:

a first nucleotide sequence transcribable to or which is an mRNA molecule, a second nucleotide sequence operatively coupled to the 5'-end of said first nucleotide sequence and effective to increase the rate of translation initiation of the mRNA molecule in a cell, and a third nucleotide sequence for a 3'-untranslated region of a gene operatively coupled to the 3'-end of said first nucleotide sequence and effective to increase the period of translation of said mRNA molecule in a cell.

The present invention may be employed to effect highly efficient translation of a wide variety of mRNA molecules, including mRNA molecules encoding a variety of proteins or peptides. Such encoded proteins or peptides may be selected from the group consisting of an enzyme, an antigen, an immunogen, an allergen, an enzyme inhibitor, a hormone, a lymphokine, an immunoglobulin or fragment thereof, a toxin, a toxin subunit, a mammalian protein, a structural protein, and a receptor.

Particular encoded proteins or peptides may include those selected from the group consisting of bovine preprolactin, human insulin receptor, α-subunit of the canine signal recognition particle receptor, the IgG binding domains of Staphylococcal protein A, HIV gag protein, CAT and HCV gB protein.

The present invention, therefore, provides a novel procedure for effecting translation of MRNA molecules in which an increased level of translation is achieved by employing a heterologous 3'-UTR.

BRIEF DESCRIPTION OF DRAWINGS

The present invention will be further understood from the following detailed description and Examples with reference to the accompanying drawings in which:

FIGS. 6 to 8 show urea-denatured gels of $^{35}$S labelled RNA after various time intervals of degradation.

FIG. 9 shows plasmid sequences used to transcribe the leaders employed herein. The SP6 promoter is marked with the thin line before the sequence. The initiation site is indicated with the thick underline. Relevant restriction sites are indicated.

IDENTIFICATION OF NUCLEOTIDE SEQUENCES

Figure 2:
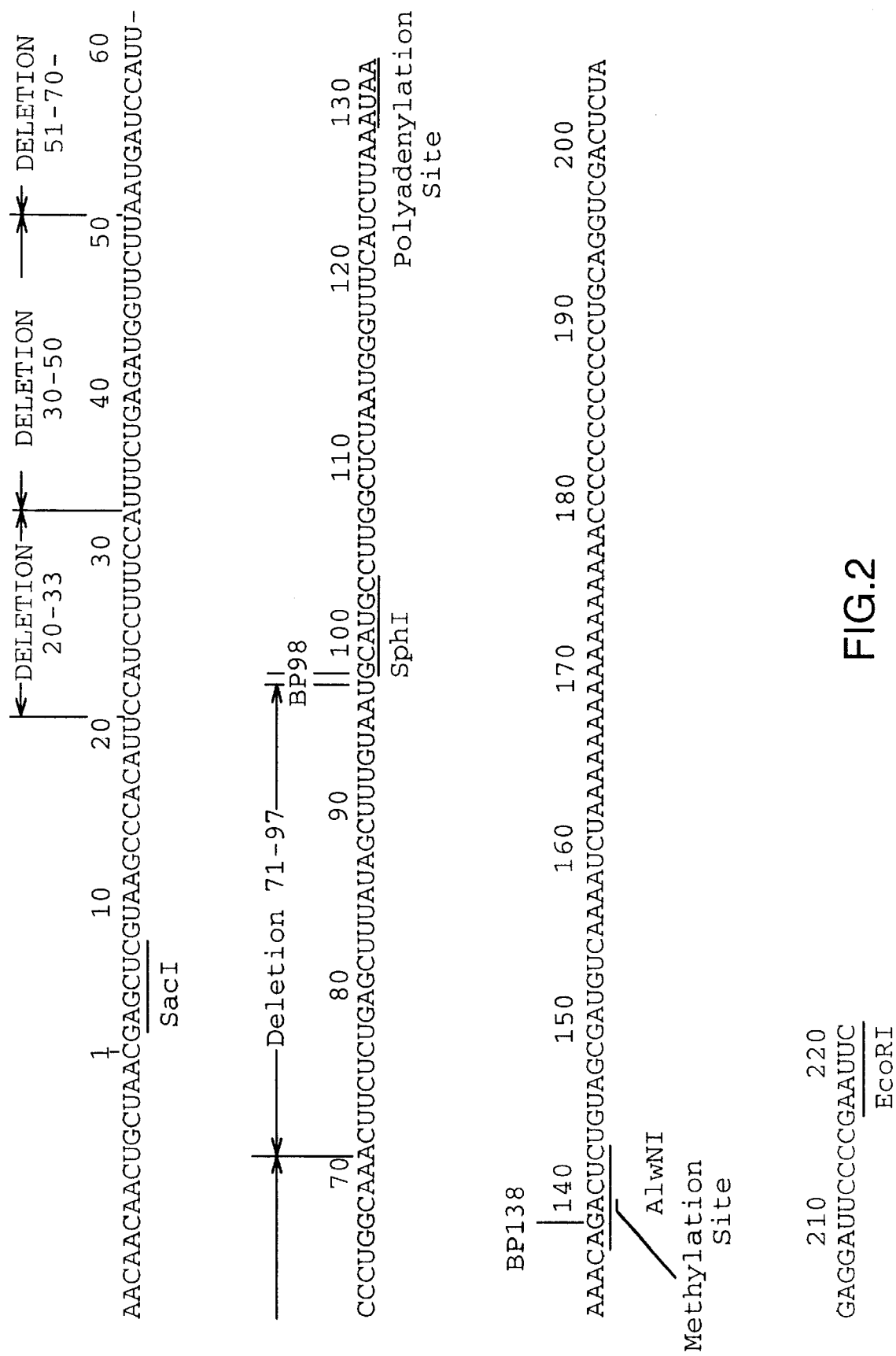
FIG. 2 shows the nucleotide sequence of the 3' UTR sequence of bovine preprolactin.

In the following Table I, the various SEQ ID Nos. are identified in relation to the nucleotide sequence as shown in FIG. 2 and the 5' leader, employed in FIG. 9.

TABLE I

| SEQ ID No: | Fragment |
|---|---|
| 1 | whole length 3' UTR |
| 2 | nucleotides 1–161 of 3' UTR |
| 3 | nucleotides 51–97 of 3' UTR |
| 4 | nucleotides 1 to EcoRI site in polylinker |
| 5 | nucleotides 1–138 of 3' UTR |
| 6 | nucleotides 1–98 of 3' UTR |
| 7 | nucleotides 1–5 of 3' UTR |
| 8 | nucleotides 1–19 and 34–98 of 3' UTR |
| 9 | nucleotides 1–19 and 34–end of 3' UTR |
| 10 | nucleotides 1–33 and 51–98 of 3' UTR |
| 11 | nucleotides 1–33 and 51–end of 3' UTR |
| 12 | nucleotides 1–50 and 71–98 of 3' UTR |
| 13 | nucleotides 1–50 and 71–end of 3' UTR |
| 14 | nucleotides 1–70 of 3' UTR |
| 15 | nucleotides 1–70 and 98–end of 3' UTR |
| 16 | ATTTAGGTGACACTATAGAATACAAGCTCATGG |
| 17 | ATTTAGGTGACACTATAGAATACAAGCTGATCTACCATGG |
| 18 | ATTTAGGTGACACTATAGAATACAAGCTTG CTTGTTCTTTTTGCAGAAGCTCAGAATAAA CGCTCAACTTTGGCAGATCCATGG |
| 19 | ATTTAGGTGACACTATAGAATACAAGCTTG CTTGTTCTTTTTGCAGAAGCTCAGAATAAA CGCTCAACTTTGGCAGATCTACCATGG |
| 22 | UGUAGCGAUGUCAAAAUAUUGUUGAAAGU |

GENERAL DESCRIPTION OF THE INVENTION

To examine mRNA stability for actively translated mRNAs in vivo, the inventors have injected in vitro transcribed RNAs with the UTK 5' leader into Xenopus oocytes. Protein synthesis was examined for four coding regions, namely bovine preprolactin (Pt), human insulin receptor, deletion mutants of bovine preprolactin and the α-subunit of the signal recognition particle (SRP) receptor. Usually RNA injected into oocytes is actively translated for less than 24 hours. However, when the amount of prolactin secreted by microinjected oocytes was examined as an indication of steady static synthesis, secretion was observed for up to 6 days following mRNA injection. The inventors have demonstrated that the 3' UTR of bovine preprolactin contains transferable sequences responsible for maintaining the injected RNA in a translation-competent form in the cytosol of Xenopus oocytes. In addition, the inventors have found that at least one regulatory sequence contained in the 3' UTR is independent of the poly (A) tail.

The inventors have shown, as demonstrated in the Examples below and discussed further below, that an mRNA can be both highly translated and stable by employing a 3' UTR region. Truncations of the 3' UTR of prolactin dramatically prolong translation for RNAs encoding Pt, SR1 and insulin receptor.

Referring to FIG. 1, there is shown a comparison of the translation of the preprolactin deletion mutant Pt with different leader sequences in Xenopus oocytes. In vitro synthesized transcripts were normalized for RNA content by fluorometry, mixed with an equal volume of [$^{35}$S] methionine and injected into Xenopus oocytes. Oocytes were incubated for 4 hours in ND96 medium, homogenized and subjected to immunoprecipitation with anti-ovine prolactin antiserum (panel A). The products of the immunoprecipitation were separated by SDS-PAGE and fluorographed. The 5' untranslated region (5'UTR) is indicated below each lane and a summary of the leaders is shown in FIG. 9. SD leader is a standard plasmid sequence, as a negative control and not imparting any particular RNA translation stimulation. The KD leader contains the standard plasmid sequence and a Kozak consensus sequence (ACCAUGG SEQ ID NO: 20) as the initiation site. The insertion of this Kozak sequence increased, the rate of translation initiation as shown by the increased amount of Pt in lane 2. The leader UTR contains the Xenopus β-globin untranslated region and an unfavourable translation initiation site (CCCAUGG SEQ ID No: 21). This leader resulted in a level of RNA translation approximately equivalent to the KD leader in lane 3. The leader UTK, contains the Xenopus β-globin untranslated region and an appropriately positioned Kozak consensus sequence as the initiation site. This semi-synthetic leader sequence is optimized for RNA translation as shown by the high level of translation Pt in lane 4. To further demonstrate the high level of translation efficiency imparted upon an mRNA by the inclusion of the Xenopus β-globin untranslated region and an appropriately positioned Kozak consensus sequence, these sequences were coupled to the 5' end of an mRNA encoding preprolactin and expressed from Xenopus oocytes. As shown in panel B of FIG. 1, prolactin continued to be synthesized and secreted into the medium for more than 60 hours post-injection. The level of prolactin secreted into the medium during a 24 hour period reached 125 ng per cell. At such a high level of expression, it was possible to detect the secretion of prolactin from oocytes by Coomassie blue staining of total culture medium after SDS-PAGE analysis. Typically the half-life for protein synthesis from an efficiently translated RNA after injection into Xenopus oocytes is a few hours (refs. 14, 23). In contrast, functional RNA encoding preprolactin persists for approximately 100 hours when the mRNA has the xenopus β-globin untranslated region and an appropriately positioned Kozak consensus sequence coupled to the 5'-end thereof. Furthermore, since microinjected oocytes survive in culture for only 5–6 days it was possible that cell viability rather than RNA stability eventually limits the synthesis of preprolactin in these cells.

Figure 3:
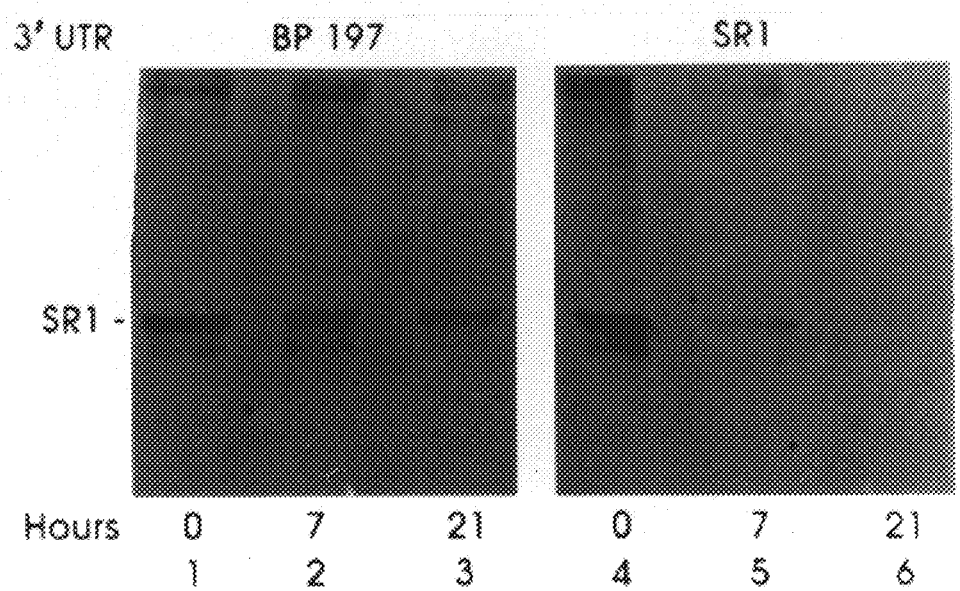
FIG. 3, comprising two panels, labeled 3A and 3B shows analysis by SDS-PAGE and fluorography of immunoprecipitated SRI synthesized in Xenopus oocytes using SR1 and BP197 3'-UTR with the migration position of SR1 being to the left of the Figure.

To demonstrate that the preprolactin 3' UTR prolonged the translation of mRNAs encoding heterologous gene products, translation of RNAs encoding either a deletion mutant of the SRP receptor α-subunit termed SR1 or preproinsulin receptor was determined. The sequence bovine preprolactin gene is shown in FIG. 2 (SEQ ID NO: 2). Both coding regions were coupled at the 5'-end thereof to the UTK leader sequence and at the 3'-end thereof to the complete 3' UTR (BP197) (SEQ ID NO: 4). The SR1 3' UTR contains coding sequences as well as 406 nucleotides of the SRP receptor α-subunit 3' UTR. When the BP197 (SEQ ID NO: 4) sequence was fused to the SR1 coding sequence in place of this 3' UTR translation of the microinjected mRNA was extended by approximately 20 hours, (10 fold) FIG. 3, compare lanes 1–3 with 4–6.

The human insulin receptor has been expressed previously in oocytes but the level of expression was so low that it was only detectable on SDS-PAGE gels after in vitro labelling of the β-subunit with [γ-$^{32}$P]ATP (ref. 49). The expression of this molecule was increased by replacing the endogenous 5' leader with either the 5' UTK leader or the 5' UTK leader with added the BP197 3' UTR to the 3' UTR of the preproinsulin receptor sequence so that a composite 3' UTR (EBP) consisting of both the BP197 3' UTR and the 3' UTR of preproinsulin was produced.

Figure 4:
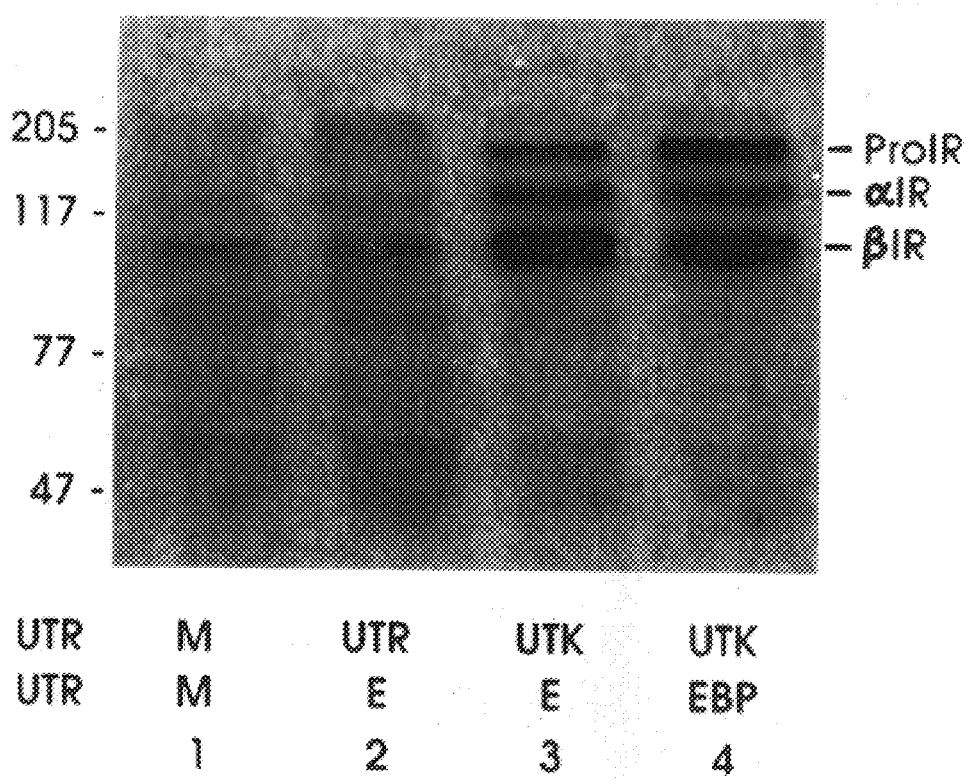
FIG. 4 shows analysis by SDS-PAGE and fluorography of immunoprecipitated insulin receptor synthesized by Xenopus oocytes. The migration position of the proreceptor, α-subunit and β-subunit of the insulin receptor are indicated to the right of the Figure. The migration positions of molecular weight markers (in kDa) are indicated at the left of the Figure.

Thus, referring to FIG. 4, there is illustrated the effect of these 5' UTR replacements and 3' UTR additions to the translation of insulin receptor mRNA in Xenopus oocytes. Oocytes were injected with 50 nl/oocyte in vitro synthesized transcript, and incubated in 1 mCi [$^{35}$S] methionine/10 ml ND96 for 24 hours. The medium was replaced with fresh medium and incubation continued for another 16 hours. Immunoprecipitated insulin receptor translation products were analyzed for sets of 6 oocytes by SDS-PAGE and fluorography. Lane 1 shows, control oocytes mock-injected with water. The 3' untranslated regions are indicated as: E, endogenous 3' UTR, EBP, fusion of the endogenous and BP197 3' UTRs. The UTR and UTK 5' leader sequences are defined above. The migration positions of the proreceptor, α-subunit and β-subunit of the insulin receptor are indicated to the right of FIG. 4. The migration positions of molecular weight markers (in kDa) are indicated at the left of FIG. 4.

In continuously labelled cells addition of the UTK leader dramatically improved the synthesis of the insulin receptor. As a result the early translation product (proreceptor) and the processed α and β subunits are easily detected by immunoprecipitation of homogenates prepared from microinjected oocytes (FIG. 4 compare lanes 2 and 3). Although addition of the BP197 3' UTR did not significantly change the amount of the processed subunits observed, the amount of proreceptor detected 40 hours post-injection was increased by 3 fold (FIG. 4 compare the top bands in lanes 3 and 4). This increase in proreceptor synthesis indicates that the mRNA encoding preproinsulin receptor is translated for a longer time when the BP197 3' UTR is coupled thereto.

To particularly localize the sequences within the BP197 3' UTR (SEQ ID NO: 4) responsible for increasing the period of translation of an mRNA molecule coupled thereto a series of mutants containing progressive deletions was constructed and analyzed. The plasmid encoding Pt with the UTK leader and BP197 3' UTR was used for these experiments as Pt is not secreted from oocytes thereby simplifying the measurement of protein synthesis at different time points. This plasmid was digested with restriction enzymes that cut the plasmid within the 3' UTR at the positions indicated in FIG. 2 and transcript was synthesized in vitro and injected into oocytes. At different times after injection oocytes were pulse labelled with [$^{35}$S] methionine for 4–5 hours. The relatively long pulse time ensured that the label completely equilibrated within the cell (ref. 41).

Figure 5:
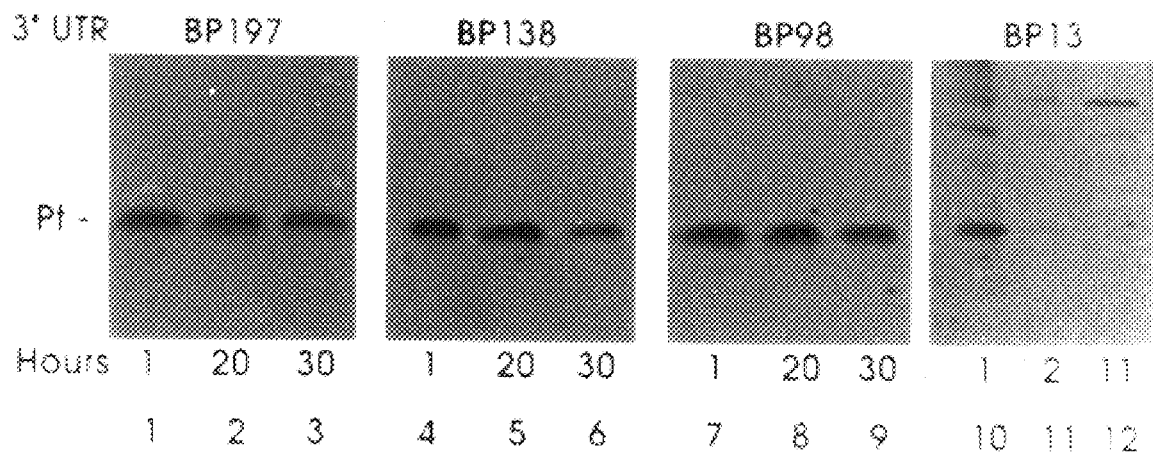
FIG. 5, comprising four panels, labeled 5A, 5B, 5C and 5D shows analysis by SDS-PAGE and fluorography of immunoprecipitated Pt synthesized from transcripts containing truncated 3'-UTRs as indicated above the panels. The migration position of Pt is indicated to the left of the Figure.
Figure 10A:
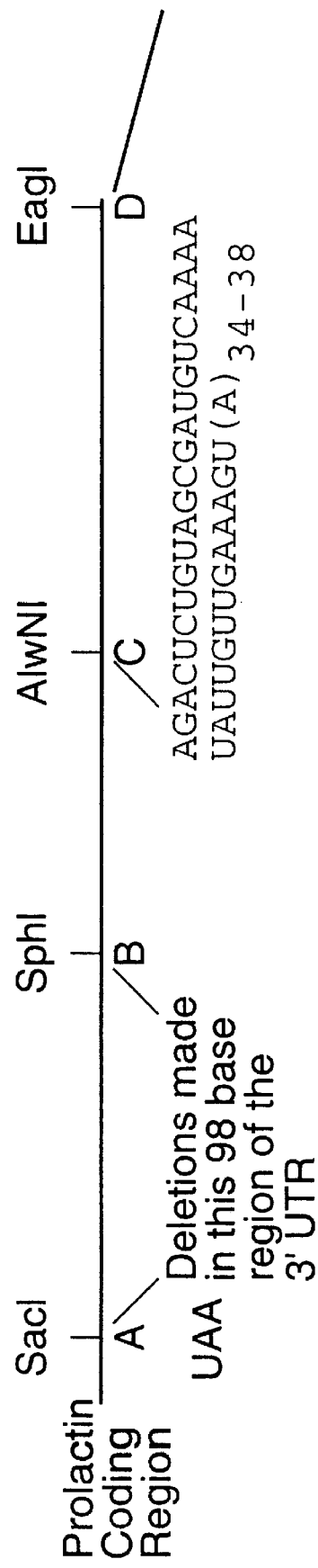
FIG. 10 shows, in the upper portion thereof, labelled I restriction sites of the 3'-UTR region of preprolactin and sequence modification from the sequence shown in FIG. 2 (SEQ ID NO: 22) and polydenylation (Poly A) tail, and, in the lower portion thereof, in graphs labelled II–V the effect of deletions in the 3'-UTR of preprolactin on the stability of polyadenylated RNA.
Figure 10B:
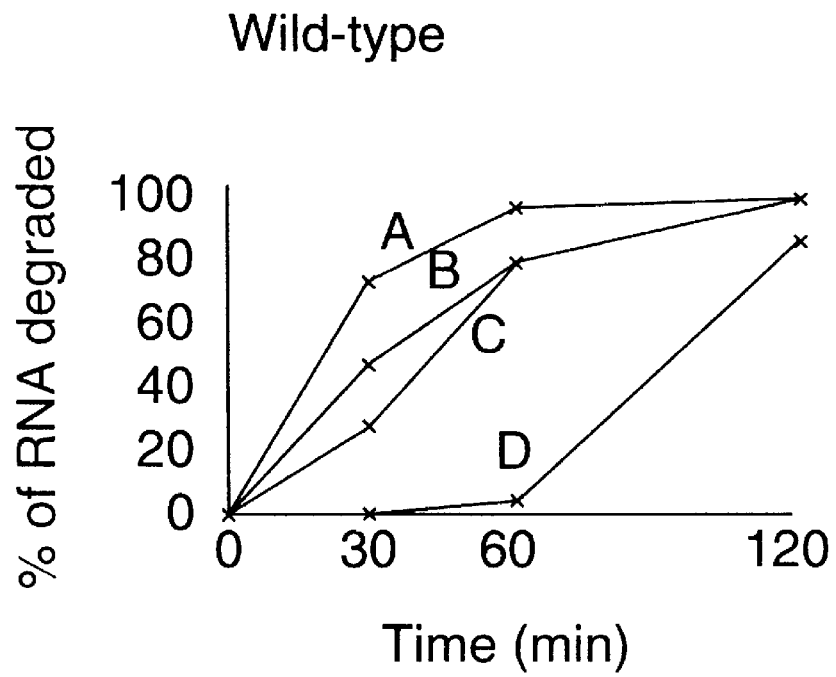
Figure 10C:
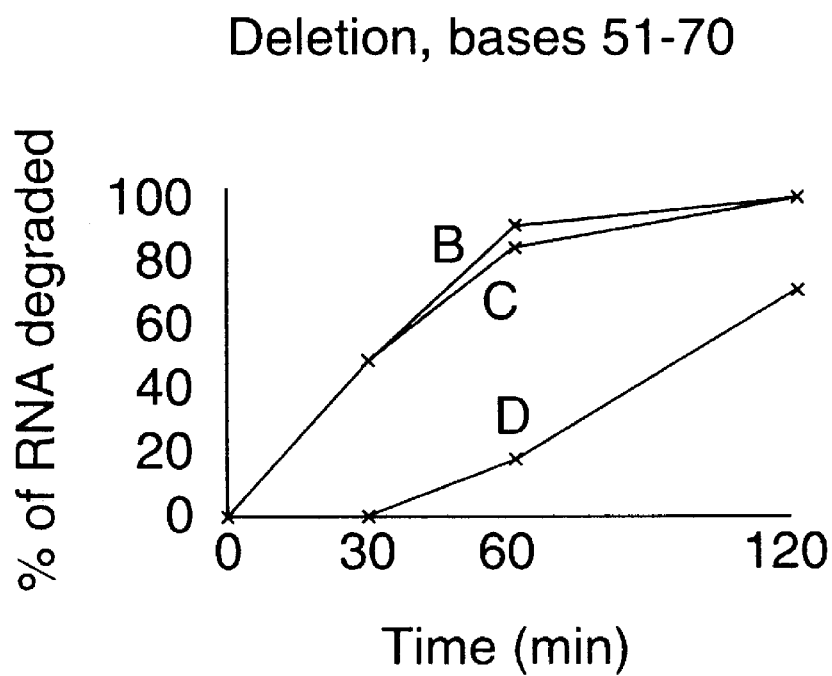
Figure 10D:
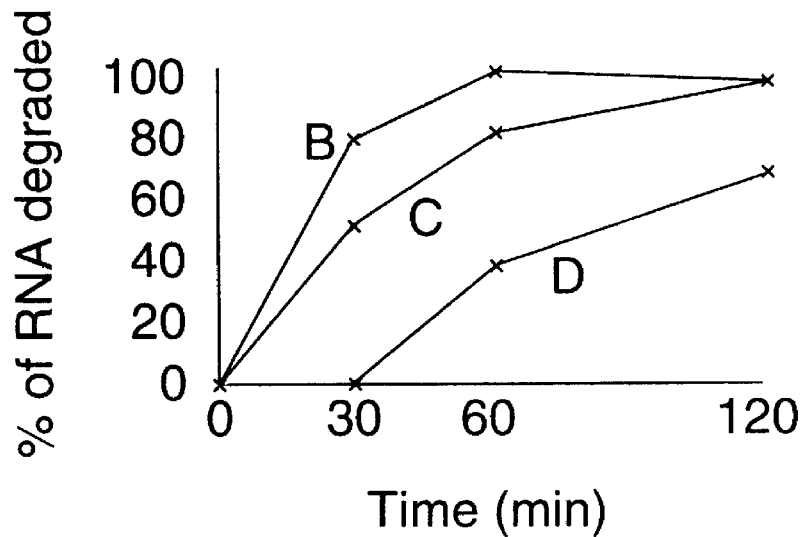
Figure 10E:
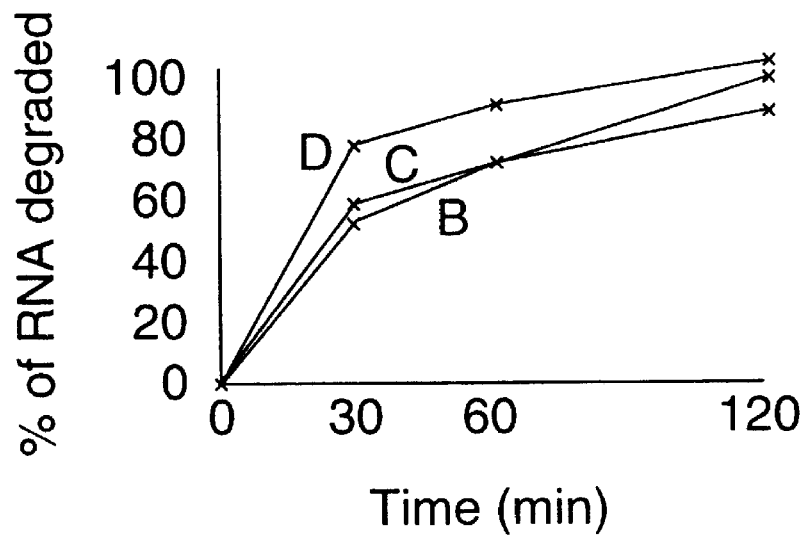

Referring to FIG. 5, there is illustrated the truncation of such mRNAs having 3' UTR. The truncations are as follows:

|  | Nucleotides in 3' UTR | SEQ ID NO: |
| --- | --- | --- |
| B197 | No truncation | 4 |
| BP138 | 1–138 | 5 |
| BP98 | 1–98 | 6 |
| BP13 | 1–5 | 7 |

Normalized transcript was injected into cells and then at the time point indicated below each lane a set of 5 oocytes was placed in media containing [$^{35}$S] methionine (0.5mCi/ 10 ml) and labelled for 5 hours. After labelling, oocytes were homogenized and translation products were immunoprecipitated with anti-ovine prolactin antiserum and separated by SDS-PAGE. The gels were fluorographed, dried and exposed to film. The migration position of Pt is indicated to the left of FIG. 5.

Comparison of the amount of Pt synthesis 30 hours after RNA injection revealed that deletion of the 3' end of the sequence (to produce BP138) (SEQ ID NO: 5), lacking the poly A tail present in the full-length sequence, reduced the translational half-life of the injected RNA somewhat (FIG. 5 lanes 3, 6, 9). In this experiment the half lives for translation of the RNA with the BP138 and BP98 3' UTRs were both approximately 30 hours. In contrast, only about 20% of the RNA with the BP197 3' UTR was inactive 30 hours post-injection.

Molecules with the BP98 3' UTR do not contain the poly A sequence, methylation site or a polyadenylation signal yet the RNA was remarkably stable (measured translational half-life about 30 hours). Translation of molecules with the BP13 3' UTR could not be detected in oocytes 2 hours post-injection (FIG. 5, lane 11). The construct containing the BP13 3' UTR ends with an EcoRI restriction site therefore, the last 5 bases in the UTR are identical to the last five bases of BP197.

RNA from another plasmid containing a 38 nucleotide 3' UTR between the stop codon and an EcoRI linearization site was also translated for less than two hours, indicating that the short length of BP13 3' UTR does not account for the differences observed in FIG. 5. Taken together, these results suggest that there is a sequence within the first 98 bases of the BP197 3' UTR that prolongs translation of RNAs in Xenopus oocytes.

To further localize the sequence within the BP197 3' UTR (SEQ ID NO: 4) further deletions were made from the 3' -UTR as shown in FIG. 2.

The translation promotion demonstrated in oocytes was reflected by greater mRNA stability in vitro RNA degradation system, which directly measures the mRNA stability. The truncations made are as follows:

|  | Nucleotides in 3' UTR | SEQ ID NO: |
| --- | --- | --- |
| Sac I | 1–5 | 7 |
| Sph I | 1–98 | 6 |
| EcoRI | No truncation | 4 |
| SphI/ deletion 20–33 | 1–19; 34–98 | 8 |
| ECORI/ deletion 20–33 | 1–19; 34–end of 3' UTR | 9 |
| SphI/ deletion 34–50 | 1–33; 51–98 | 10 |
| EcORI/ deletion 34–50 | 1–33; 51–end of 3' UTR | 11 |
| SphI/ deletion 51–70 | 1–50; 71–98 | 12 |
| EcoRI/ deletion 51–70 | 1–50; 71–end of 3' UTR | 13 |
| SphI/ deletion 71–97 | 1–70; | 14 |
| EcoRI/ deletion 71–97 | 1–70; 98–end of 3' UTR | 15 |

Referring to FIGS. 6, 7 and 8 there is illustrated the stability of such truncated mRNAs by a degradation assay. Details of this assay appears in Example 7 below.

RNA was produced by in vitro transcription using SP6 RNA polymerase. Radiolabelling of the RNA was achieved by including $^{35}$S -UTP at a concentration of 100 nM in the transcription mix.

The degradation assay is based upon a Rabbit Reticulocyte Lysate preparation. The preparation is not subjected to nuclease or gel-filtration treatment. Radiolabelled RNA was incubated in a buffered mixture-containing lysate, Creatine Kinase and 'E-mix' (containing all 20 amino acids, Creatine Phosphatase, ATP and GTP). The degradation assay was stopped at time points following the start of the reaction by the addition of Vanadyl Ribonucleoside Complexes, and then snap-frozen in liquid nitrogen. RNA was recovered by Phenol/Chloroform extraction followed by ethanol precipitation. Resuspended RNA was then analyzed on a TBE/urea denaturing acrylamide gel, which was then dried and exposed to autoradiography film.

FIG. 6 shows the effect of incubating radiolabelled RNA, synthesized from SacI (SEQ ID NO: 7), SphI (SEQ ID NO: 8) or EcoRI (SEQ ID NO: 4) truncated plasmids, in the degradation assay for 0, 30, 60 or 120 min. In keeping with the data obtained for the Xenopus oocytes, it can be seen that the SacI product is unstable, decaying such that it has disappeared after 60 min. The SphI product is more stable, decaying after 120 min. The EcoRI product, however, is still stable after 120 min.

FIGS. 7 and 8 show the degradation patterns of the RNA's created by further deletions. Deletions of the nucleotides between positions 20–33 (SEQ ID NO: 8, 9) and 34–50 (SEQ ID NO: 9, 11) produce essentially the same pattern as seen for wild type. Deletions between nucleotides 51–70 (SEQ ID NO: 12, 13) and 71–97 (SEQ ID NO: 14, 15) causes no difference in stability when the DNA template is truncated at the SphI site. However, the transcript produced when the template is truncated at EcoRI (SEQ ID NO: 15) is much less stable in both cases than is wild type. Thus, there are nucleotides between positions 51 and 97 which contribute to the stability of the mRNA molecule.

EXAMPLES

The above disclosure generally describes the present invention. A more complete understanding can be obtained by reference to the following specific Examples. These Examples are described solely for the purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, and immunology used but not explicitly described in this disclosure and these Examples are amply within the ability of those skilled in the art.

Example 1

This Example describes construction of certain plasmids.

A plasmid encoding the α-subunit of SRP receptor was modified by introducing a termination codon (in an XbaI linker) into the coding region at codon 426. The plasmid was then cut with XbaI, and repaired with the Klenow fragment of polymerase and a SacI linker was added. These manipulations resulted in a plasmid encoding the deletion mutant SR1, containing the first 426 amino acids of SRP receptor α-subunit with a SacI site immediately following the termination codon. Thus, the SR1 3' UTR contains 636 nucleotides of coding sequence and 406 nucleotides of the SRP receptor α-subunit 3' UTR. The insulin receptor plasmid contains 180 nucleotides of the endogenous 3' UTR ending with an SpeI restriction site. For cloning purposes the plasmid was cut with SpeI, end repaired using the Klenow fragment of DNA polymerase and a SacI linker was inserted.

Construction of plasmids encoding either preprolactin or the preprolactin deletion mutant Pt with the SD, KD, UTR and UTK leaders were described previously (ref. 38). Sequences for these leaders (SEQ ID NOS: 16–19) are shown in FIG. 9. The complete 3' UTR and coding region of Pt is similar to that of preprolactin, except that amino acids 2 to 58 of the mature prolactin domain have been deleted. In addition, a SacI restriction site was introduced immediately following the termination codon of Pt using the naturally occurring EspI site overlapping the termination codon. The translation start site in the UTK leader is contained within an NcoI site as seen in FIG. 9. By first removing the SacI site in the polylinker sequence at the 3' end of the Pt construct, it was possible to replace the Pt coding region in this plasmid with other coding sequences by digestion with NcoI and SacI. The resulting plasmids contained the desired coding region flanked with the UTK leader and the bovine preprolactin 3' UTR. Plasmids containing the insulin receptor and SR1 coding regions were assembled in this way. To construct plasmids with the UTK leader and the endogenous 3' UTR use was made of a plasmid (PSPUTK, available from Stratagene) containing the UTK leader followed by a multiple cloning site. The 3' and 5' ends of the constructs were sequenced using the NEB vent polymerase sequencing system according to the manufacturers instructions.

Example 2

This Example describes transcription of mRNA in vitro.

Plasmids prepared as described in Example 1 were linearized by digestion with a suitable restriction enzyme before transcription in vitro (ref. 39). In most cases, an EcoRI restriction site within the polylinker at the 3' end of the 3' UTR was used for linearization. Restriction sites within the preprolactin 3' UTR were used to produce transcripts truncated at different positions within the 3' UTR.

Because SphI and AlwNI leave 3' overhangs, the DNA was end repaired using the Klenow fragment of DNA polymerase prior to transcription in vitro (ref. 39). Sp6 polymerase reactions generating capped transcripts were as described previously except that glutathione buffer (50 mM reduced glutathione, 10 mM oxidized glutathione and 20 mM Hepes pH 7.5) was used in place of DTT (ref. 40). Transcripts were normalized for RNA contents using a fluorometric assay described previously (ref. 33). An aliquot of each transcript was translated in a reticulocyte lysate reaction prior to injection to ensure that full length molecules were synthesized from the RNA. Reticulocyte lysate translations were effected as described previously (ref. 38) and contained 1 $\mu$l of the transcription reaction and 10 $\mu$Ci [$^{35}$S] methionine.

Example 3

This Example illustrates translation of mRNA in Xenopus oocytes.

Adult female breeding *Xenopus laevis* were purchased from Boreal (St. Catharines, Canada). Ovarian fragments were surgically removed from anaesthetized animals, stage VI oocytes were manually dissected and stored at 19° C. in ND96 media (96 mM NaCl, 2 mM KCl, 1 mM MgCl, 1 mM CaCl, 5 mM Hepes, pH 7.6) supplemented with antibiotics. Oocytes were injected using a model NA-1, injection system (Sutter Instrument Co. Novato, Calif.). Borosilicate micropipettes (I.D. 0.5 mm, O.D. 1.0 mm) were pulled using a K. T. Brown Type Puller and bevelled using a model BV-10 beveller (both Sutter Instrument Co. Novato, Calif.).

Translational efficiency in Xenopus oocytes was determined by co-injection of in vitro synthesized transcription products and [$^{35}$S] methionine. Normalized SP6 transcription products were mixed with an equal volume of [$^{35}$S] methionine (10 mCi/ml) and 50 nl were injected into each oocyte. Groups of 40 to 50 oocytes were injected with each transcript and incubated in ND96, for the time indicated. To assess the period of translational activity of the injected RNA, transcript was injected alone and cells were pulse labelled at the indicated times by placing 5 to 10 oocytes in 0.5 ml ND96 containing [$^{35}$S] methionine (0.05 mCi/ml) for 4 or 6 hours for Pt and SR1 transcripts respectively. To follow insulin receptor expression, [$^{35}$S] methionine was present during the entire 40 hour incubation.

After incubation, oocytes were homogenized and the labelled proteins were recovered by immunoprecipitation as described (ref. 27) except for SR1 translation products where the solubilization and initial wash buffer contained 1.5% Triton X-100, 500 mM NaCl, 100 mM Tris-Cl pH 8.0, 10 mM EDTA, the mouse IgG1 monoclonal antibody (ref. 42) was precipitated using an equal mixture of protein A and protein G agarose, and the initial pelleting step was over a 0.5M sucrose cushion. Antibodies to ovine prolactin and human insulin receptor (AB-1) were obtained from United States Biochemicals (Cleveland, Ohio), and Oncogene Science, (Uniondale, N.Y.) respectively. Protein A coupled to agarose was purchased from BioRad Laboratories (Mississauga, Canada) and protein G coupled to agarose from Oncogene Science (Uniondale, N.Y.).

Figures 1A, 1B:
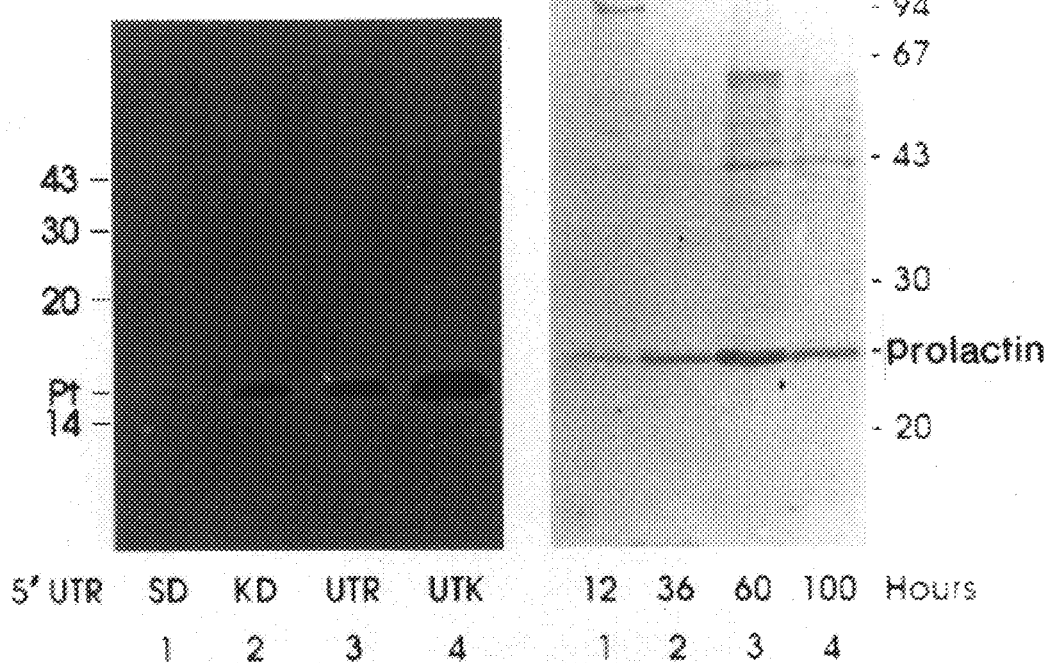
FIG. 1A shows analysis by SDS-PAGE and fluorography of immunoprecipitated Pt synthesized in injected xenopus oocytes, with the migration positions of Pt and molecular weight markers indicated to the left of panel.
FIG. 1B shows visualization of prolactin secreted by Xenopus oocytes by Coomassie blue staining.

Immunoprecipitation products were separated by SDS-PAGE using the Tris-tricine buffer system, fluorographed and exposed to film (ref. 43). Relative protein synthesis was quantified by densitometer. The results obtained are shown in FIG. 1A.

Example 4

This Example contains a discussion of the level of MRNA translation.

Previously there was reported that the UTK leader increased the rate of translation initiation for a variety of coding regions in vitro (ref. 38). The previous in vitro results have been extended to an in vivo whole cell system. To this end, transcription products from SP6 polymerase reactions were injected into Xenopus oocytes and protein synthesis was examined by immunoprecipitation of the prolactin deletion mutant Pt, from cells labelled with $^{35}$S methionine as described in Example 3. The 5' leader sequences used were the same as examined previously (ref. 38) and were selected to permit comparison of the effect on translation of the UTR sequence with that of the consensus sequence for translation initiation (ref. 44). The SD and KD leaders contain plasmid derived sequence between the SP6 promoter and the translation start site and therefore are typical of the untranslated sequences obtained using most standard cloning vectors. The translation start sites for the SD and KD leaders are the relatively unfavourable initiation sequence CCCUAGG (SEQ ID NO: 21) and the strong initiation sequence ACCAUGG (SEQ ID NO: 20) respectively (ref. 45). The UTR and UTK leaders contain the Xenopus β-globin 5' UTR linked to these compromised and strong initiation sequences respectively.

To assay the translational efficiency of the different leaders in a whole-cell system, transcription products were injected into Xenopus oocytes, as described in Example 3. Microinjection permits direct comparison of different RNA's translation independent of transcription. In addition, the differences observed are unlikely to be influenced by rates of maturation of transport, from the nucleus because the RNA is injected directly into the cytoplasm. Microinjection of RNA containing the UTK leader into oocytes resulted in more synthesis of Pt during a four hour pulse label than was obtained for RNA with the other leaders, FIG. 1A. Moreover, both the UTR and the consensus sequence for translation initiation contributed to the increase in protein synthesis observed (FIG. 1A, compare lanes 2 and 3 with 4). Densiometry for five separate experiments indicated that the increase in translation efficiency due to addition of the consensus initiation sequence was approximately the same as that due to the UTR sequence (3 to 4 fold). The net increase due to the two sequences together was greater than 7 fold indicating that the two sequences independently promote efficient translation.

The observation that regions in the 5' UTR increase translation efficiency independently from the consensus sequence for efficient initiation, (FIG. 1A) is not predicted by the scanning model for initiation (ref. 46). The scanning model states that the nucleotide sequence immediately surrounding the initiator AUG is the primary determinant of translational efficiency and does not allow for regions of the 5' UTR being involved in enhancing translation (ref. 33). However, the Xenopus 5' UTR clearly increased translational efficiency even for mRNAs with a compromised initiation sequence in diverse systems and Xenopus oocytes indicating that this region acts as a general enhancer of eukaryotic translation.

After microinjection of preprolactin RNA containing the UTK leader into Xenopus oocytes, the amount of protein secreted into the medium during a 24 hour period was as high as 125 ng per cell. Therefore, it was possible to detect the secretion of prolactin from oocytes by Coomassie blue staining of total culture medium after SDS-PAGE, as seen in FIG. 1B. Most of the preprolactin labelled in a 4 hour pulse was secreted as prolactin from the oocytes within 6 hours (ref. 27). It is surprising that prolactin secretion could be detected by Coomassie blue staining of total oocyte media up to 6 days following infection of the RNA (FIG. 1B). Typically the half-life for protein synthesis from an efficiently translated RNA after injection into Xenopus oocytes is a few hours (refs. 15, 16). In contrast, densitometry of the data obtained from three independent experimentation similar to that shown in FIG. 1B revealed that functional RNA encoding preprolactin persists for at least 100 hours. Because microinjected oocytes survive in culture for only 5 to 6 days it is possible that cell viability rather than RNA stability eventually limits the synthesis of preprolactin in these cells.

The functional half-life of a coding region is often determined by sequences within the 31 UTR (refs. 13, 17). The nucleotide sequence and other salient features deduced from the DNA sequence of the prolactin 3' UTR are shown in FIG. 2 (SEQ ID NO: 1). DNA sequencing of this region revealed that the poly A sequence is followed by a run of 10 C's. Although this sequence is not part of the authentic preprolactin 3' UTR as it was added during the initial cDNA cloning of preprolactin, it was part of the 3' UTR assayed above, and was therefore included in the constructs described herein. The preprolactin 3' UTR contains a nuclear polyadenylation sequence but lacks the cytoplasmic polyadenylation element necessary for addition of A residues in the cytoplasm of Xenopus oocytes (ref. 47). Other previously characterized motifs such as the AU-rich motif known to destabilize a wide variety of mRNAs (ref. 19) are absent from the preprolactin 3' UTR. However, the sequence does contain 4 repeats of the sequence CCAU.

Example 5

This Example illustrates the use of preprolactin 3' UTR to prolong translation of heterologous mRNA.

Protein synthesis was measured for hybrid RNAs encoding either a deletion mutant of the SRP receptor α-subunit termed SR1 or preproinsulin receptor. Both coding regions were flanked by the UTR leader sequence and the complete 3' UTR (BP197—SEQ ID NO: 4). The SR1 3' UTR contains coding sequences as well as 406 nucleotides of the SRP receptor α-subunit 3' UTR. When the BP197 sequence was fused to the SR1 coding sequence in place of this 3' UTR translation of the microinjected RNA was extended by approximately 20 hours, (10 fold), as seen in FIG. 3, compare lanes 1 to 3 with 4 to 6. Although the SR1 3' UTR contains coding sequences, the period during which the injected RNA is translated (FIG. 3, lanes 4 to 6) is similar to that of other injected RNAs. The apparent stability of the hybrid RNA is due to prolonged translation of the species with the BP197 3' UTR rather than rapid degradation of the RNA with the SR1 3' UTR.

The human insulin receptor has been expressed previously in oocytes but was only detectable on SDS-PAGE gels after in vitro labelling of the β-subunit with [γ-$^{32}$P]ATP (ref. 26). To improve expression of the human insulin receptor, the endogenous 5' leader was replaced with the UTK leader and the BP197 3' UTR was added to the 3' UTR of the preproinsulin receptor sequence. In continuously labelled cells, addition of the UTK leader dramatically improved the synthesis of the insulin receptor. As a result, the early translation product (proreceptor) and the processed α and β subunits are easily detected by immunoprecipitation of homogenates prepared from microinjected oocytes (as seen in FIG. 4, compare lanes 2 and 3). Although addition of the BP197 3' UTR did not significantly change the amount of the processed subunits observed, the amount of proreceptor detected 40 hours post injection was increased by 3 fold (see FIG. 4, compare the top bands in lanes 3 and 4). The increase in proreceptor synthesis results from the mRNA encoding preproinsulin receptor being translated for a longer time when fused to the BP197 3' UTR.

Example 6

This Example illustrates the effect of modifications to the preprolactin 3' UTR on mRNA translation.

A series of mutants containing deletions from BP197 3' UTR were examined (SEQ ID NOS: 5–7 for these mutations identified in Table 1 above). The plasmid encoding Pt with the UTK leader and BP197 3' UTR was used for these experiments as Pt is not secreted from oocytes, thereby simplifying the measurement of protein synthesis at different time points. This plasmid was digested with restriction enzymes that cut the plasmid within the 3' UTR at the positions indicated in FIG. 2, the transcript was synthesized in vitro and injected into oocytes. At different times after injection, oocytes were pulse labelled with [$^{35}$S] methionine for 4 to 5 hours. The relatively long pulse time ensured that the label completely equilibrated within the cell (ref. 16).

Comparison of the amount of Pt synthesis 30 hours after RNA injection revealed that deletion of the 3' end of the sequence reduced the translational half-life of the injected RNA somewhat (see FIG. 5, lanes 3, 6, 9). In this experiment, the half-lives for translation of the RNA with the BP138 and BP98 3' UTRs were both approximately 30 hours. In contrast, only about 20% of the RNA with the BP197 3' UTR was inactive 30 hours post-injection. The additional sequences within the BP197 3' UTR included a sequence of 17 A's followed by 10 C's and the predominant site of methylation in vivo (ref. 48). Based on previous observations that a poly A tail containing 32 A's but not 17 A's was sufficient for mRNA stability it is unlikely that the poly A sequence contributes significantly to RNA stabilization (ref. 18).

Molecules with the BP98 3' UTR do not contain the poly A sequence, methylation site or a polyadenylation signal, yet the RNA was remarkably stable (measured translational half-life 30 hours). In contrast, other RNAs microinjected into Xenopus oocytes are found only in non-polycomal fractions within 4 hours of deadenylation (ref. 47). Consistent with these results translation of molecules with the BP13 3' UTR could not be detected in oocytes 2 hours post-injection (see FIG. 5, lane 11). The construct containing the BP13 3' UTR ends with an EcoRI restriction site, therefore, the last 5 bases in the UTR are identical to the last five bases of BP197. RNA from another plasmid containing a 38 nucleotide 3' UTR between the stop codon and an EcoRI linearization site was also translated for less than 2 hours indicating that the short length of the BP13 3' UTR does not account for the differences observed in FIG. 5. Taken together, these results indicate that there is a sequence within the first 98 bases of the BP197 3' UTR that prolongs translation of RNAs in Xenopus oocytes.

Example 7

This Example describes a degradation assay for determining the stability of mRNAs.

Radioactive RNA was prepared as follows:

Plasmid DNA was linearized with an appropriate restriction enzyme. The enzyme was then heat killed at 70° C. for 20 min. Where necessary, the DNA was treated with Klenow Fragment. Proteins were removed by phenol/chloroform extraction, the DNA was precipitated with ethanol and then resuspended in TE buffer. For transcription, 1 $\mu$l (approx. 1 $\mu$g) of linearized DNA is incubated with:

2 $\mu$l CB5X
2 $\mu$l NTP mix
1 $\mu$l $^{35}$S-UTP
1 $\mu$l DTT
0.2 $\mu$l tRNA
0.4 $\mu$l RNAguard
0.4 $\mu$l SP6 RNA polymerase (10 $\mu$l$^{-1}$)
2 $\mu$l MQ Water
for 1 h at 37° C.

Degradation assay

Radioactive RNA was incubated in a degradation assay mix at 24° C. for varying lengths of times. The degradation assay was set up as follows:

0.5 $\mu$l CB20X (linked)
4.2 $\mu$l Rabbit Reticulocyte Lysate
2.0 $\mu$l "E-mix"
0.1 $\mu$l Creatine Kinase (4mg ml$^{-1}$)
1.0 $\mu$l radioactive RN
2.2 $\mu$l MQ Water Degradation was halted by the addition of 2 $\mu$l 200 mM Ribonucleoside-Vanadyl Complex (NEB), and then snap-frozen in liquid nitrogen.

RNA was recovered from the mix by phenol/chloroform extraction and ethanol precipitation. Precipitated nucleic acids was resuspended in 3 $\mu$l of TE buffer. Formamide denaturing loading buffer was added to 9 $\mu$l total, and the sample was heated at 70° C. for 10 min. Of the sample, 6 $\mu$l were analyzed on a TBE/urea acrylamide gel. Following the run, the gel was dried and exposed to autoradiographic film.

The various buffers used in this assay were prepared as follows:

|  | RRL | | WG | |
| --- | --- | --- | --- | --- |
|  | vol | final [ ] | vol | final [ ] |
| 1M HEPES-KpH 7.5 | 400 $\mu$L | 80 mM | 400 $\mu$L | 80 mM |
| 1M MgCl$_2$ | 75 $\mu$L | 15 mM | | |
| 1M MgAc$_2$ | | | 70 $\mu$L | 14 mM |
| 0.1M spermidine | 100 $\mu$L | 2 mM | 100 $\mu$L | 2 mM |
| water | 425 $\mu$L | | 430 $\mu$L | |
| total | 1 mL | | 1 mL | |
| 4 NTP (5×) | uncapped | | capped | |
| 0.1M ATP | 150 $\mu$L | | 150 $\mu$L | |
| 0.1M CTP | 150 | | 1.50 | |
| 0.1M UTP | 150 | | 150 | |
| 0.1M GTP | 150 | | 15 | |
| water | 400 | | 535 | |
| total | 1 mL | | 1 mL | | adjust pH to 7.0 with 2 Tris base.

Example 8

This Example illustrates the effect of deletions in the 3' UTR region on the stability of polyadenylated RNA.

Plasmids were constructed as described in Example 1 in which the 17-nucleotide stretch of adenine residues followed 11-nucleotide stretch of cytidine residues at the 3' end from nt 161 to 189 was replaced by a short linker sequence and a longer poly (A) tail containing uniquely adenine residues by fusing the poly (A) tail from another coding region onto the 3' end of the preprolactin 3' UTR, providing the construction seen in the upper part of FIG. 10 (panel I). In addition, internal deletion mutants were prepared as described above by PCR mediated deletion of bases 51 to 70, 66 to 80 and 71 to 98.

Plasmids were linearized by digestion with a suitable restriction enzyme and transcribed in vitro as described in Example 2. The transcripts were allowed to undergo degradation over time and the results for the variously constructed 3' UTR molecules were plotted graphically, as seen in the lower part of FIG. 10, labelled I to IV.

These results confirm the stability results described in the preceding Examples. The 3' UTR region with poly A tail provide a stable transcript, while removal of the 3' UTR region and poly A tail resulted in an unstable transcript.

Truncating the template prior to transcription at the SacI site (panel I, site A) results in an RNA molecule which is extremely unstable. Following only 30 min. incubation, about 80% of the RNA has been degraded with complete degradation being achieved after 60 min (panel II (wild-type) curve A). Truncations at the SphI and AlwNI sites (panel I, sites B and C respectively), result in RNA molecules which are more stable than that produced when truncated at the SacI site (compare panel II, curve A to curves B and C at the 30 and 60 min time points). There is no significant difference between curves B and C for any of the deletions made in the SacI to SphI regions (compare panels II, III and IV and V). Since curves B and C are essentially identical, it can be concluded that there is an element in the 3' UTR positioned between the SacI and SphI sites (rather than between the SphI and AlwNI sites) which confers stability to the RNA molecule, independent of the poly(A) tail, which is not affected by small deletions in this region.

mRNA molecules consist, in addition to the 5' UTR, the coding region, the 3' UTR and polyadenylation signal, a poly(A) tail. The addition of the poly(A) tail is achieved (in this case) by truncating the template after a poly(A) sequence prior to transcription (panel I, site D). As expected, the mRNA molecule is more stable than the non-polyadenylated form of the same molecule (panels II, III and IV, compare curve D to curves B and C). Examining the difference between the mRNA molecules harbouring deletions between the SacI and SphI site revealed a portion of the molecule which is required for maximum stability of the polyadenylated mRNA. The wild type molecule (panel II), together with deletions up to nucleotide 50 (data not shown), deletion 51–70 (panel III), and 66–80 (panel IV) show the poly(A) tail increased stability of the mRNA molecules compared to RNA that does not contain a poly (A) tail (compare curve D to curves B and C). A deletion between bases 71–89, however, abolishes the stabilizing effect on the poly(A) tail, and renders the molecule as unstable as the non-poly(A) tail deletions (panel V, compare curve D to curves B and C). As this effect was not seen for deletion 66–80 (panel IV), it can, therefore, be concluded that there is an element, situated between bases 81 and 98, which increases the stability of RNA containing a poly(A) tail.

Thus, it is shown by this data that (a) non-poly(A) mediated stability by a sequence situated between the SacI and SphI site (bases 1 through 98 of the prolactin 3' UTR), and overlaps (b) a specific sequence located between bases 81 and 98 which confers stability to the polyadenylated mRNA.

These results indicate that a degradation system specific for mRNA is blocked by the stabilization sequence contained in the 3'-UTR region.

SUMMARY OF THE DISCLOSURE

In summary of this disclosure, the present invention provides a novel method of promoting translation of an mRNA molecule in a cell using nucleotide sequences provided at 5' and 3' ends of itself or the mRNA molecule itself a nucleic acid molecule transcribable to the mRNA molecule, so as to increase the rate of translation initiation of the mRNA molecule and to increase the period of translation thereof. Modifications are possible within the scope of this invention.

REFERENCES

| REFERENCES |
|---|
| 1. Cigan, A. M., and T. F. Donahue. (1987) Gene 59, 1–18. |
| 2. Kozak, M. (1988) J. Cell Biol. 107, 1–7. |
| 3. Lodish, H. F. (1976) Ann. Rev. Biochem. 45, 39–72. |
| 4. Liebhaber, S. A., F. Cash and S. S. Eshleman. (1992) Journal of Molecular Biology 226, 609–621. |
| 5. Sorenson, M. A,, C. G. Kurland and S. Pedersen. (1989) J. Mol. Biol. 207, 365–377. |
| 6. Sharp, P. M., and K. M. Devine. (1989) Nucleic Acids Res. 17, 5029–5039. |
| 7. Baim, S. B. and F. Sherman. (1988) Mol. Cell. Biol. 8, 1591–1601. |
| 8. Doohan, J. P. and C. E. Samuel. (1992) Virology 186, 409–425. |
| 9. Kim, J., P. G. Klein and J. E. Mullet. (1991) J. Biol. Chem., 266, 14931–14938. |
| 10. Kim, J., M. J. Hollingsworth. (1992) Anal. Biochem. 206, 183–188 |
| 11. Rabinovich, Y. M. and M. O. Kreinin. (1991) Biochimica et Biophysica Acta 1089, 193–196. |
| 12. Young, J. H. C., A. Vassilakos and D. W. Andrews, submitted. |
| 13. Saini, K. S., I. C. Summerhayes and P. Thomas (1990) Mol, Cell. Biochem. 96, 15–23. |
| 14. Jackson, R. J. (1993) Cell 74, 9–14. |
| 15. Drummond, D. R., J. Armstrong and A. Colman. (1985) Nucleic Acids Res. 13, 7375–7394. |
| 16. Nudel., tJ., H. Soreq and U. Z. Littauer. (1976) Eur. J. Biochem, 64, 115–121. |
| 17. Bernstein, P. and J. Ross. (1989) TIBS 14, 373–377. |
| 18. Galili, G., E. E. Kawata, L. D. Smith and B. A. Larkins (1988) J. Biol. Chem. 263, 5764–5770. |
| 19. Jacksori, R. J. and N. Standart. (1990) Cell 62, 15–24. |
| 20. Wickens, M. (1990) TIBS 15, 320–324. |
| 21. Laird-offringa, I. A., C. A. deWit, P. Elfferich and A. J. van der Eb. (1990) Mol. Cell. Biol. 10, 6132–6140. |
| 22. Aharon, T. and R. J. Schneider. (1993) Mol. Cell. Biol. 13, 1971–1980. |
| 23. Ratnasabapathy, R., S. L. Hwang and D. L. Williams. (1990) J. Biol. Chem. 265, 14050–14055. |
| 24. Saini, K. S. and I. C. Summerhayes. (1991) Biochem. Cell, Biol. 69, 415–417. |
| 25. Brawerman, G. (1989) Cell 57, 9–10. |
| 26. Pelham, H. R. B. (1978) Eur. J. Biochem. 85, 457–462. |
| 27. Pelletier, J. and N. Sonenberg. (1988) Nature 334, 320–325. |
| 28. Jobling, S. A. and L. Gehrke. (1987) Nature 325, 622–625. |
| 29. Jobling, S. A., C. M. Cuthbert, S. G. Rogers, R. T. Fraley and L. Gehre. (1988) Nucleic Acids Res. 16, 4483–4498 |
| 30. Johansen, H., D. Schumperli and M. Rosenberg. (1984) Proc. Natl. Acad. Sci. USA 81, 7698–7702. |
| 31. Elroy-Stein, O. T. R. Fuerst and B. Moss. (1989) Proc. Natl. Acad. Sci. USA 86, 6126–6130. |
| 32. Gallie, D. R., D. E. Sleat, J. W. Watts, P. C. Turner and T. M. A. Wilson. (1987) Nucleic Acids Res. 15, 3257–3273. |

REFERENCES

33. Gallie, D. R., D. E. Sleat, J. W. Watts, P. C. Turner and T. M. A. Wilson. (1987) Nucleic Acids Res. 15, 8693–8711.
34. Berkner, K. L. and P. A. Sharp. (1985) Nucleic Acids Res. 1–3, 841–856.
35. Curran, J. and D. Kolakofsky. (1989) EMBO J. 8, 521–526.
36. Lazarus, P. (1992) Oncogene 7, 1037–1041.
37. Tyc, K., M. Konarska, H. J. Gross and W. Filipowicz. (1984) FEBS 140, 503–511.
38. Falcone, M. and D. W. Andrews. (1991) Mol. Cell. Biol. 11, 2656–2664.
39. Andrews, M. T. (1989) Promega Notes No. 17:1.
40. Gurevich, V. V., I. D. Pokrovskaya, T. A. Obukhova and S. A. Zozulya. (199 ) Anal. Biochem. 195, 207–213.
41. Simon, K., E. Perara and V. R. Lingappa. (1987) J. Cell Biol. 104: 1165–1172.
42. Tajima, S., L. Lauffer, V. L. Rath and P. Walter. (1986) J. Cell Biol. 103, 1167–1178.
43. Schagger, H. and G. von Jagow. (1987) Anal. Biochem. 166, 368–379.
44. Kozak, M. (1978) Cell 44, 283–292.
45. Kozak, M. (1987) Nucleic Acids Res. 15, 8125–8148.
46. Kozak, M. (1989) J. Cell Biol. 108, 229–241.
47. Fox, C. A. and M. Wickens. Genes Dev. 4, 2287–2298.
48. Narayan, P., Ludwiczak, R. L., Goodwin., E. C. and Rottman, F. M. (1994) Nucleic Acids Res. 22, 419–426.
49. Vera, J. C. and O. M. Rosen. (1990) Mol. Cell. Biol. 10, 743–751.

What we claim is:

1. A method of translating a selected mRNA molecule to provide an increased level of translation thereof, which comprises:
coupling to a nucleic acid molecule transcribable to or which itself is an mRNA molecule at the 5'-end thereof a first nucleotide sequence heterologous to the nucleic acid molecule and effective to increase the rate of translation initiation of said mRNA molecule in a cell,
coupling to said nucleic acid molecule at the 3'-end thereof a second nucleotide sequence heterologous to the nucleic acid molecule and comprising at least a portion of a 3'- untranslated region (UTR) of a gene and effective to increase the period of translation of said mRNA molecule in a cell, and
effecting translation of said mRNA molecule in said cell.

2. The method of claim 1 wherein said second nucleotide sequence comprises a nucleotide sequence of the 3'-UTR of a prolactin gene shown in FIG. 2 and effective to increase the period of translation of the mRNA molecule.

3. The method of claim 1 wherein said second nucleotide sequence comprises a nucleotide sequence selected from the group consisting of those of the 3'-UTR of a prolactin gene shown in Table 1 and having SEQ ID NOS: 1,3,8,9,10,11, 12 and 14 and effective to increase the period of translation of the mRNA molecule.

4. The method of claim 2 wherein said first nucleotide sequence comprises that of a β-globin 5'-UTR coupled to a translation initiation sequence.

5. The method of claim 4 wherein said β-globin is xenopus β-globin.

6. The method of claim 5 wherein said translation initiation sequence comprises a Kozak consensus sequence which is ANNAUGG.

7. The method of claim 6 wherein said consensus sequence is ACCAUGG.

8. The method of claim 6 wherein said translation initiation sequence further comprises a Shine-Dalgarno sequence.

9. The method of claim 2 wherein said second nucleotide sequence comprises at least a portion of the 3'-UTR of a prolactin gene contained within nucleotide 51 to nucleotide 97 as seen in FIG. 2 (SEQ ID NO.:3) and effective to increase the period of translation of the mRNA molecule.

10. The method of claim 9 including coupling a polyadenylation sequence to the 3'-end of said second nucleotide sequence prior to said translation step.

11. The method of claim 1 wherein said first nucleotide sequence comprises that of Xenopus β-globin coupled to a Kozak consensus sequence which is ACCAUGG.

12. The method of claim 1 wherein said cell is a prokaryotic or a eukaryotic cell.

13. A method translating a selected mRNA molecule, which comprises:
coupling to a nucleic acid molecule transcribable to or which itself is an mRNA molecule at the 3'-end thereof a nucleotide sequence heterlogous to the nucleic acid molecule and comprising at least a portion of the 3'-untranslated region (UTR) of a prolactin gene shown in FIG. 2 and effective to increase the period of translation of said mRNA molecule in a cell, and
effecting translation of said mRNA molecule in said cell.

14. The method of claim 13 wherein said nucleotide sequence comprises a nucleotide sequence selected from the group consisting of those of the 3'-UTR of a prolactin gene shown in Table 1 and having SEQ ID NOS.: 1,3,8,9,10,11,12 and 14 and effective to increase the period of translation of the mRNA molecule.

15. The method of claim 13 wherein said nucleotide sequence comprises at least a portion of the 3'-UTR of a prolactin gene contained within nucleotide 51 to nucleotide 97 as seen in FIG. 2 (SEQ ID NO.:3) and effective to increase the period of translation of the mRNA molecule.

16. The method of claim 13 including coupling a polyadenylation sequence to the 3' end of said nucleotide sequence prior to said translation step, whereby mRNA stabilization of the translated molecule is effected independently by both said nucleotide sequence and said polyadenylation sequence.

17. The method of claim 1 or 13 wherein said mRNA molecule encodes a protein or peptide.

18. The method of claim 17 wherein said protein or peptide is selected from the group consisting of an enzyme, an antigen, an immunogen, an allergen, an enzyme inhibitor, a hormone, a lymphokine, an immunoglobulin or fragment thereof, a toxin, a toxin subunit, a mammalian protein, a structural protein, and a receptor.

19. The method of claim 18 wherein said protein or peptide is selected from the group consisting of bovine preprolactin, human insulin receptor, α-subunit of the canine signal recognition particle receptor, the IgG binding domains of Staphylococcal protein A, HIV gag protein, CAT and RCV gB protein.

20. A hybrid nucleic acid molecule, comprising:
a first nucleotide sequence transcribable to or which is an mRNA molecule,
a second nucleotide sequence heterologous to the first nucleotide sequence and operatively coupled to the 5'-end of said first nucleotide sequence and effective to increase the rate of translation initiation of the mRNA molecule in a cell, and
a third nucleotide sequence heterologous to the first nucleotide sequence and comprising at least a portion of the 3'- untranslated region (UTR) of a gene and operatively coupled to the 3'-end of said first nucleotide sequence and effective to increase the period of translation of said mRNA molecule in a cell.

21. The nucleic acid molecule of claim 20 wherein said third nucleotide sequence comprises a nucleotide sequence of the 3'-UTR of a prolactin gene shown in FIG. 2 and effective to increase the period of translation of said mRNA molecule.

22. The nucleic acid molecule of claim 20 wherein said third nucleotide sequence comprises a nucleotide sequence selected from the group consisting of those of the 3'-UTR of a prolactin gene shown in Table 1 and having SEQ ID NOS.: 1,3,8,9,10,11,12 and 14 and effective to increase the period of translation of the mRNA molecule.

23. The nucleic acid molecule of claim 20 further comprising a polyadenylation sequence operatively coupled to the 3'-end of said third nucleotide sequence and effective for stabilization of translation of said mRNA in a cell independent of said third nucleotide sequence.

24. The nucleic acid molecule of claim 20 wherein said third nucleotide sequence comprises at least a portion of the 3'-UTR of a prolactin gene contained within nucleotide 51 to nucleotide 97 as seen in FIG. 2 (SEQ ID NO:3) and effective to increase the period of translation of said mRNA molecule.

25. The nucleic acid molecule of claim 20 wherein said second nucleotide sequence comprises that of a β-globin 5'-UTR coupled to a translation initiation sequence.

26. The nucleic acid molecule of claim 25 wherein said β-globin is xenopus β-globin.

27. The nucleic acid molecule of claim 26 wherein said translation initiation sequence comprises a Kozak consensus sequence which is ANNAUGG.

28. The nucleic acid molecule of claim 27 wherein said Kozak consensus sequence is ACCAUGG.

29. The nucleic acid molecule of claim 27 wherein said initiation sequence further comprises a Shine-Dalgarno sequence.

30. A hybrid nucleic acid molecule, comprising:
a first nucleotide sequence transcribable to or which is an mRNA molecule, and
a second nucleotide sequence heterologous to said first nucleotide sequence and comprising at least a portion of a 3'-untranslated region (UTR) of a gene and operatively coupled to the 3'-end of said first nucleotide sequence and effective to stabilize translation of said mRNA molecule in a cell.

31. The hybrid nucleic acid molecule of claim 30 further comprising a polyadenylation sequence operatively coupled to the 3'-end of said second nucleotide sequence and effective to stabilize translation of said mRNA molecule in a cell independent of said second nucleotide sequence.

32. The hybrid nucleic acid molecule of claim 31 wherein said second nucleotide sequence comprises a nucleotide sequence of the 3'-UTR of a prolactin gene shown in FIG. 2 and effective to increase the period of translation of the mRNA molecule.

33. The hybrid nucleic acid molecule of claim 31 wherein said second nucleotide sequence comprises a nucleotide sequence selected from the group consisting of those of the 3'-UTR of a prolactin gene shown in Table 1 and having SEQ ID NOS. 1,3,8,9,10,11,12, and 14 and effective to increase the period of translation of the mRNA molecule.

34. The hybrid nucleic acid molecule of claim 31 wherein said second nucleotide sequence comprises at least a portion of the 3'-UTR of a prolactin gene contained within nucleotide 51 to nucleotide 97 as seen in FIG. 2 (SEQ ID NO:3) and effective to increase the period of translation of said mRNA molecule.

35. The nucleic acid molecule of claim 20 or 30 wherein said mRNA molecule encodes a protein or peptide.

36. The nucleic acid molecule of claim 35 wherein said protein or peptide is selected from the group consisting of an enzyme, an antigen, an immunogen, an allergen, an enzyme inhibitor, a hormone, a lymphokine, an immunoglobulin or fragment thereof, a toxin, a toxin subunit, a mammalian protein, a structural protein, and a receptor.

37. The nucleic acid molecule of claim 36 wherein said mRNA molecule encoded protein or peptide is selected from the group consisting of bovine preprolactin, human insulin receptor, α-subunit of the canine signal recognition particle receptor, the IgG binding domains of Staphylococcal protein A, HIV gag protein, CAT and HCV gB protein.

* * * * *